United States Patent [19]

Rothman

[11] 4,069,306

[45] Jan. 17, 1978

[54] X-RAY CONTRAST PREPARATION CONTAINING A HYDROPHILIC POLYMER CONTAINING AMINO GROUPS

[75] Inventor: Ulf Sven Erik Rothman, Bjarred, Sweden

[73] Assignee: Pharmacia Aktiebolag, Uppsala, Sweden

[21] Appl. No.: 688,820

[22] Filed: May 21, 1976

Related U.S. Application Data

[63] Continuation of Ser. No. 555,221, March 4, 1975, abandoned.

[30] Foreign Application Priority Data

Mar. 14, 1974   Sweden ................................. 7403402

[51] Int. Cl.$^2$ ............................................. A61K 29/02
[52] U.S. Cl. ............................................. 424/4; 424/79
[58] Field of Search ........................ 536/112; 424/4, 79

[56] References Cited

U.S. PATENT DOCUMENTS

| 2,659,690 | 11/1953 | Slaybaugh | 424/4 |
| 2,680,089 | 6/1954 | Lowy | 424/4 |
| 2,746,906 | 5/1956 | Novak et al. | 424/4 |
| 3,002,823 | 10/1961 | Flodin et al. | 536/112 X |
| 3,236,735 | 2/1966 | Brown | 424/4 |
| 3,277,025 | 10/1966 | Flodin et al. | 536/112 X |
| 3,539,682 | 11/1970 | Eriksson | 424/4 |
| 3,627,872 | 12/1971 | Parkinson | 424/79 |
| 3,784,681 | 1/1974 | Fischler | 424/4 |
| 3,846,541 | 11/1974 | Howard | 424/79 |
| 3,980,770 | 9/1976 | Ingelman et al. | 424/79 |

FOREIGN PATENT DOCUMENTS

| 478,108 | 1/1938 | United Kingdom | 424/4 |
| 998,331 | 7/1965 | United Kingdom | 424/4 |
| 1,108,348 | 4/1968 | United Kingdom | 424/4 |

Primary Examiner—Albert T. Meyers
Assistant Examiner—Vera C. Clarke
Attorney, Agent, or Firm—Fred Philpitt

[57] ABSTRACT

An X-ray contrast preparation comprising a) a finely divided water-insoluble inorganic X-ray contrast producing substance and b) minute particles of a hydrophilic polymer containing amino groups, which polymer is insoluble in water at body temperature and which consists of a water-insoluble, but water-swellable three-dimensional network held together by bonds of a covalent nature, said polymer containing a certain amount of amino groups and the average particle size of the polymer particles lying within a certain range. The preparation is intended for the X-ray examination of body cavities having outer discharge orifices. It adheres very effectively to the walls of the body cavities.

8 Claims, No Drawings

X-RAY CONTRAST PREPARATION CONTAINING A HYDROPHILIC POLYMER CONTAINING AMINO GROUPS

This is a continuation of application Ser. No. 555,221, filed Mar. 4, 1975, now abandoned.

The present invention relates to an X-ray contrast preparation comprising an inorganic, finely divided X-ray contrast producing agent, such as barium sulphate, and an additive in the form of certain polymer particles. The invention also relates to the novel use of such polymer particles as an additive in such X-ray contrast preparations.

The X-ray contrast preparation according to the present invention is intended for the examination of body cavities having outer discharge orifices, such as the alimentary tract. It was earlier known to use, for example, finely divided barium sulphate suspended in water as an X-ray contrast agent for such X-ray examinations. It was also known to add to a barium sulphate suspension, different water-soluble or water-insoluble substances, such as gum arabic, alginic acid, carboxymethyl cellulose, pectin and cellulose particles and flavouring substances, these substances being added, for example, to increase the stability of the suspension, to influence the speed at which the contrast agent passes the intestines, to influence the adherence of said agent to the mucous membranes and to improve its taste.

In many cases insufficient information, or at times no information, is obtained regarding possible changes in the state of the stomach and intestines of a patient, when examining the same by means of X-rays, using conventional contrast agents. This is due, among other things, to the fact that the contrast agent does not effectively cover the walls of the body cavities, and neither does said agent remain adhered to said walls for a sufficiently long period of time, even though the intestines may have been previously emptied. Thus, X-ray pictures taken on the walls of the stomach and intestines are not sufficiently detailed despite the fact that, in many cases, the so-called double contrast technique is applied. In many cases, the contrast agent crackles in the intestines, agglomerates are formed and the agent adheres to the contents of the intestines, such as faeces, which impairs the examination. Because of this, and because of other deficiencies, it is often necessary to recall a patient for re-examination, which is obviously a disadvantage, both medically and economically.

An object of the present invention is to provide preparations whereby these, and other disadvantages may be at least substantially eliminated.

The X-ray contrast preparation according to the present invention comprises a finely divided water-insoluble inorganic X-ray contrast producing substance, and the preparation is mainly characterized in that it also comprises minute particles of a hydrophilic polymer containing amino groups which polymer is insoluble in water at body temperature and which consists of a water-insoluble, but water-swellable three-dimensional network held together by bonds of a covalent nature said polymer containing more than 0.01 and less than 20 milliequivalents of amino groups per gram of dry polymer, wherein the average particle size of the polymer particles in the presence of water is greater than 0.01 micrometer and smaller than 500 micrometer.

The terms "insoluble in water" and "water-insoluble" used hereinafter in connection with the inorganic contrast producing substance are intended to include both such substances that are completely insoluble in water as well as those which are sparingly soluble in water.

The term "amino groups" refers here and in the claims to amino groups in the wide sense, and thus includes primary, secondary and tertiary amino groups as well as quaternary amino groups. In accordance with a suitable embodiment of the invention, the outer layer of the polymer particles contain amino groups, although said groups may also be present in the interior of said particles. The amino groups may be present, either wholly or partially in the form of a non-toxic salt. In general, the amino groups are at least partially converted to such salts, so that X-ray contrast preparations containing the small particles, the X-ray contrasting agent and water, obtain a suitable pH for introduction into the body cavities. Examples of such physiologically acceptable (non-toxic) salts include salts with mineral acids, such as hydrochloric acid and sulphuric acid and organic acids, for example low molecular weight carboxylic acids and hydroxycarboxylic acids, which yield non-toxic salts.

In accordance with the invention, the minute polymer particles and the X-ray contrasting agent may be suspended in water or in some other aqueous physiologically acceptable liquid. Preferably the body cavity is supplied with such a preparation obtained by suspending said minute polymer particles in water, the X-ray contrasting agent being present in mixture with and/or enclosed in and/or adhered to said minute particles, wherein the pH of the suspension is, when necessary, adjusted to a value suitable for introduction of said suspension into said body cavity, for example a pH of 5 – 8. The preparation may also be admixed with physiologically acceptable substances, such as salts, e.g. sodium citrate and sodium chloride, agents which influence the function of the stomach and/or the intestines, therapeutical substances, substances which raise the viscosity, e.g. gum arabic and carboxymethyl cellulose, anti-foam agents, e.g. dimethylpolysiloxane, and flavouring substances. When required, antimicrobial substances may be added, to prevent the growth of micro-organisms. When the preparation is intended for the X-ray examination of the stomach, antacid can be added, if required. The preparation may be sterilized, for example by heat-treatment processes. The suspension may be pre-prepared in the factory, or may be prepared at the place where the X-ray examination is to be carried out, by suspending said minute particles and the finely-divided X-ray contrasting agent in water or in some other suitable aqueous physiologically acceptable liquid.

In the presence of water, the average particle size of the minute polymer particles may be of the order of magnitude less than 500 $\mu$m(micrometer), preferably less than 300 $\mu$m, e.g. less than 200 $\mu$m or less than 100 $\mu$m. In general, in the presence of water the average particle size may be of an order of magnitude which is greater than 0.01 $\mu$m, preferably greater than 0.1 $\mu$m, preferably greater than 0.5 $\mu$m, generally greater than 1 $\mu$m or greater than 5 $\mu$m or greater than 20 $\mu$m. The polymer particles may have a substantially spherical form or may be of irregular shape.

The ionizable amino groups in the polymer particles give rise to positive surface charges on the particles in the presence of water. The walls of the body cavities are covered by the small polymer particles together with the finely divided X-ray contrasting agent in mixture with and/or enclosed in and/or adhered to said minute polymer particles, owing to the fact that said particles adhere to the walls of the cavities. The extent to which the contrast agent adheres to the contents of the intestines, such as faeces, is less than that with previously known contrast agents. In accordance with a particularly suitable embodiment of the invention, the surface layer of the small polymer particle contains amino groups in a quantity such that the net surface charge of said particles is positive in the liquid present in the body cavity during the course of the X-ray examination. Thus, the surface layer of the minute polymer particles may contain, for example, amino groups in a quantity such that the surface charge of the particles is positive in aqueous liquids having a pH of 7. In accordance with one embodiment of the invention, the only ionizable groups on the surface layers of the minute polymer particles are amino groups. In accordance with a second embodiment of the invention, the surface layers of the minute polymer particles contain more amino groups than other ionizable groups which give rise to negative surface charges, e.g. carboxyl groups, sulpho (sulphonic acid) groups or other groups which give rise to negative surface charges.

In accordance with the invention, the polymer particles contain amino groups, suitably in the surface layers thereof. From the aspect of preparation, it is simplest if both the outer surfaces of the polymer particles and the inner parts thereof contain amino groups. The amino groups are bound to the polymer by means of bonds of a covalent nature, the amino groups either being present as links in the basic skeleton of the three-dimensional network or projecting therefrom. The amino groups may also be obtained in the surface layers of the polymer particles, by providing the particles with substituents containing amino groups.

The hydrophilic groups in the polymer may be the amino groups. In accordance with a suitable embodiment of the invention, the polymer contains also hydroxyl groups, whereby the water-insoluble polymer obtains advantageous hydrophilic properties.

In accordance with the invention, the polymer may comprise a cross-linked polymeric or polymerized carbohydrate or sugar alcohol, which is substituted with amino groups. Thus, the three-dimensional network of the polymer may suitably consist of a cross-linked polysaccharide substituted with amino groups.

As aforementioned, the polymer is insoluble in water at body temperature, i.e. around 37° C. It is, however, also insoluble in water in the temperature range of from 0° C to 40° C. Preferably, the polymer is stable and also insoluble in water at still higher temperatures, such as for example 60° C or 80° C or 100° C or 120° C. By selecting polymers which are insoluble in water at 100° C or 110° C or 120° C, the polymer particles may be sterilized in aqueous suspension by subjecting them to a heat-treatment process (for example autoclaving).

In accordance with the aforegoing, the amino groups in the polymer particles may be primary and/or secondary and/or tertiary and/or quaternized amino groups. Suitably the amino groups are chosen so that the major part thereof are secondary and/or tertiary and/or quaternary amino groups, preferably tertiary and/or quaternized amino groups.

The swellability of the polymer particles in water may be such that one gram (1 g) of polymer in the presence of water is able to absorb more than 0.5 g of water, e.g. more than 1 g of water, such as more than 2 g of water and less than 50 g of water, e.g. less than 20 g of water, such as less than 10 g of water.

The present invention also relates to the novel use of the above mentioned minute polymer particles as an additive to X-ray contrast preparations intended for the X-ray examination of body cavities having outer discharge orifices, said X-ray contrast preparations comprising a finely divided waterinsoluble inorganic X-ray contrast producing substance.

The X-ray contrast producing agent used is primarily barium sulphate, since good results are obtained herewith when practicing the invention in, for example, the X-ray examination of the alimentary tract, especially the stomach and the intestines. Other finely-divided inorganic X-ray contrast agents which are insoluble or sparingly soluble in water may be used in the inventive X-ray contrast preparation for said purpose. Examples of such agents include certain metals having a high atomic weight and certain compounds of such metals, for example tantalum and bismuth compounds. Barium sulphate is preferably used, however.

Barium sulphate in finely divided form, e.g. having an average particle size of the order of magnitude of 0.01 – 100 $\mu$m, such as 0.1 – 30 $\mu$m, e.g. 0.5 – 10 $\mu$m, is readily mixed with the minute polymer particles. Finely divided barium sulphate may also be enclosed in the polymer particles by being mixed therewith during the preparation of said particles, or by precipitating the barium sulphate by means of barium ions and sulphate ions in the polymer particles when said particles have a suitable porous structure. Finely divided barium sulphate used for said X-ray contrast preparation may, furthermore, adhere to the polymer particles in question. A good suspension stability and flowability can be obtained for suspensions of barium sulphate and the minute particles in water or aqueous liquid according to the invention. Such preparations are therefore also relatively simple to administer.

The minute polymer particles may, for example, be prepared from polysaccharides, such as dextran, cellulose, starch and pollulan and derivatives thereof (for example polysaccharides substituted by lower hydroxyalkyl groups) crosslinked by means of bridges with bonds of a covalent nature to a water-insoluble three-dimensional network, for example with the aid of bifunctional or trifunctional cross-linking agents, such as epichlorohydrin or diepoxides or corresponding halaohydrins or diisocyanates or diisothiocyanates or dicarboxylic acid dichlorides or other bridge-forming dicarboxylic acid derivatives etc. and substituted with amino-containing groups, e.g. diethylaminoethyl groups or other dialkylaminoalkyl groups and/or with such groups which are quaternized, e.g. which are quaternized by means of an alkylating agent, e.g. an epoxide or a halohydrin, such as ethylene oxide, propylene oxide, glycidol or 2-chloroethanol and $\alpha$-monochlorohydrin. Such products are found described, for example, in the British Patent Specifications Nos. 936,039 and 1,013,585.

The polymer may thus comprise, for example, dextran or starch cross-linked with epichlorohydrin and substituted with amino groups, for example dialkylaminoalkyl groups, such as diethylaminoethyl groups, which amino groups may also be quaternized with an alkylating agent, e.g. propylene oxide or glycidol.

Other examples of polymers relevant in this context include those described in the Swedish Patent Specifications Nos. 360,366 and 360,367 and other, similar water-insoluble but water-swellable polymers obtained by cross-linking polyfunctional amines, such as triethylene tetraamine and tetraethylene pentaamine and other polyethylene amines with bridgeforming agents, such as epichlorohydrin or diepoxides, such as 1,4-butanedioldiglycide ethers. Other examples of such polymers include the aforementioned polymers containing amino groups in which said groups are wholly or partially quaternized, e.g. with the aid of propylene oxide or other alkylating agents.

For the preparation of polymers consisting of a practically infinite three-dimensional network (containing amino groups or substituted with groups containing amino groups), which may be used to advantage in accordance with the invention, multifunctional substances containing, for example, —OH and/or $$-\overset{|}{N}H$$

groups, for example polymeric or polymerized carbohydrates and sugar alcohols, especially polysaccharides and polysaccharide derivatives, or polyfunctional amines (for example di- or polyamines such as hexamethylenediamine and tetraethylene pentamine and other polyethylene amines) may be reacted with at least bifunctional bridge-forming agents, for example of the type $$X \cdot A_1 \cdot Z \text{ (I)} \quad \text{and} \quad X \cdot \overset{Y}{\underset{}{A_2}} \cdot Z \text{ (II)}$$

in which X, Y and Z each represent a halogen atom, preferably chloro or bromo, and $A_1$ and $A_2$ each represent a straight or branched aliphatic, saturated hydrocarbon chain substituted by one or more (e.g. 1 - 10, for example 1 - 4) hydroxyl groups, said chain containing preferably 3 - 30 carbon atoms, e.g. 3 - 20 carbon atoms, and which chain is optionally broken by one or more (e.g. 1 - 10, for example 1 - 4) oxygen atoms, or corresponding epoxide compounds obtainable by splitting off hydrogen halide from the compound (I) or (II). As examples of bifunctional substances of the formula X . $A_1$ . Z and corresponding epoxide compounds which are obtainable by splitting off hydrogen halide from the compound X . $A_1$ . Z can be mentioned the following:

$$CH_2\text{—}CH\text{—}CH_2 . O . (CH_2)_{n_1} . O . CH_2 . CH\text{—}CH_2$$
$$\diagdown O \diagup \qquad\qquad\qquad\qquad \diagdown O \diagup$$

where $n_1$ is an integer from 2 to 4, and $$CH_2\text{—}CH.CH_2.O.CH_2.CH_2.O.CH_2.CH_2.O.CH_2.CH\text{—}CH_2$$
$$\diagdown O \diagup \qquad\qquad\qquad\qquad\qquad\qquad \diagdown O \diagup$$

and $$CH_2\text{—}CH . CH_2 . O . \overset{CH_3}{\underset{|}{CH}} . CH_2 . CH_2 . O . CH_2 . CH\text{—}CH_2$$
$$\diagdown O \diagup \qquad\qquad\qquad\qquad\qquad \diagdown O \diagup$$

and $$CH_2\text{—}CH . CH_2 . O . CH_2 . CH\text{—}CH_2$$
$$\diagdown O \diagup \qquad\qquad \diagdown O \diagup$$

and

-continued $$CH_2\text{—}CH . CH_2 . O . CH_2 . CH(OH) . CH_2 . O . CH_2 . CH\text{—}CH_2$$
$$\diagdown O \diagup \qquad\qquad\qquad\qquad\qquad\qquad \diagdown O \diagup$$

or corresponding halohydrins, and bifunctional glycerol derivatives of the formula X . $CH_2$ . CH(OH) . $CH_2$ . Z, for example dichlorohydrin and dibromohydrin or corresponding epoxide compounds of the formula $$CH_2\text{—}CH . CH_2 . Z$$
$$\diagdown O \diagup$$

obtainable by splitting off hydrogen halide, e.g. epichlorohydrin and epibromohydrin. Another example of such a bifunctional compound is 1,2 - 3,4-diepoxibutane of the formula $$CH_2\text{—}CH . CH\text{—}CH_2.$$
$$\diagdown O \diagup \quad \diagdown O \diagup$$

Examples of trifunctional bridge-forming agents which are epoxide compounds which correspond to compounds of the formula $$X . \overset{Y}{\underset{}{A_2}} . Z \text{ are}$$

$$CH_2\text{—}CH . CH_2 . O . CH_2 . \overset{|}{\underset{CH_2 . CH\text{—}CH_2}{CH}} . CH_2 . O . CH_2 . CH\text{—}CH_2$$
$$\diagdown O \diagup \qquad\qquad \overset{}{\underset{\diagdown O \diagup}{}} \qquad\qquad \diagdown O \diagup$$

The polyfunctional substances are reacted with a sufficient quantity of an at least bifunctional bridge-forming agent to obtain a water-insoluble gel, i.e., a practically infinite three-dimensional network.

The bridges in the three-dimensional network, may, for example, be straight or branched aliphatic saturated hydrocarbon chains substituted by one or more (e.g. 1 - 10, for example 1 - 4) hydroxyl groups, said chains preferably containing 3 - 30 carbon atoms, for example 3 - 20 carbon atoms, and being optionally broken by one or more (e.g. 1 - 10, for example 1 - 4) oxygen atoms. The bridges may thus, for example, have the formula:
—$CH_2.CH(OH)$—$CH_2$— or
—$CH_2.CH(OH).CH(OH).CH_2$— or
—$CH_2.CH(OH).CH_2.O.CH_2.CH(OH).CH_2$— or
—$CH_2.CH(OH).CH_2.O.CH_2.CH_2.O.CH_2.CH(OH).CH_2$— or
—$CH_2.CH(OH).CH_2.O.(CH_2)_4.O.CH_2.CH(OH).CH_2$— or
—$CH_2.CH(OH).CH_2.O.CH_2.CH_2.O.CH_2.CH_2.O.CH_2.CH(OH).CH_2$— or
—$CH_2.CH(OH).CH_2.O.CH_2.CH(OH).CH_2.O.CH_2.CH(OH).CH_2$— or $$-CH_2.CH(OH).CH_2.O.\overset{CH_3}{\underset{|}{CH}}.CH_2.CH_2.O.CH_2.CH(OH).CH_2-$$

or
—$CH_2.CH(OH).CH_2.O.CH_2.CH(OH).CH_2.O.(CH_2)_4.O.CH_2.CH(OH).CH_2.O.CH_2.CH(OH).CH_2$—.

When the polymer, for example, comprises a cross-linked polysaccharide the above mentioned bridges may be bound to the polysaccharide chains by ether linkages. When the polymer comprises cross-linked polyamines the above mentioned bridges may be directly bound to nitrogen atoms in said polyamines.

Such polymers may be readily substitued with groups which contain amino groups (or substituted with additional amino groups if the polymer already contains amino groups), for example, by reacting the polymers with diethylaminoethyl chloride or other alkylating agents containing amino groups, or with an acylating agent containing amino groups. The amino groups may be fully or partially quaternized, if desired.

The amino groups are present in the polymer in a quantity such that they correspond, for example, to more than 0.01, e.g. more than 0.1, such as more than 0.5, e.g. more than 1 milliequivalent of amino groups per gram of dry polymer, and e.g. less than 20, generally less than 15, e.g. less than 10, e.g. less than 6, e.g. less than 4 milliequivalents of amino groups per gram of dry polymer.

The polymer particles, for example, contain amino groups, so that the ion exchange capacity is greater than 0.01, e.g. greater than 0.1, such as greater than 0.5, e.g. greater than 1 and lower than 20, generally lower than 15, e.g. lower than 10, such as lower than 6, e.g. lower than 4 milliquivalents of chloride ions, calculated per gram dry polymer particles.

The ratios between the contrast-producing agent and the polymer particles may be varied within wide limits, and are dependent on the contrast-producing agent and the polymer particles chosen, as well as on the size and swellability of the particles in water and on the desired density of the contrast-producing agent. Suitable and optimal proportions between the selected contrast-producing agent and the selected polymer particles can be readily discovered by those skilled in this art, and the correct amount of water may readily be added to obtain the desired density of the suspension.

For example, for 100 grams of contrast-producing substance, preferably barium sulphate, the amount of polymer particles (calculated as dry particles) may be more than 0.5 g, e.g. more than 2 g, such as more than 3 g, e.g. more than 5 g, and less than 500 g, e.g. less than 100 g, such as less than 50 g, e.g. less than 30 g. When examining the intestines by means of X-rays using a preparation of barium sulphate and the polymer particles described in Example 1 below, suitable conditions are obtained with more than 2 g and less than 30 g of polymer particles per 100 g of the finely divided barium sulphate used, and optimal conditions are obtained within the range of 5 to 20 g in the test described in said Example.

The polymer particles and the inorganic contrast producing substance are suspended in water or a physiologically acceptable aqueous liquid, said contrast substance being present in an effective contrast producing amount. The suspension of polymer particles and inorganic contrast producing substance may contain, for example, 0.2 – 40 g, preferably 0.4 – 20 g, e.g. 1 – 10 g of the polymer particles and, for example, 5 – 100 g, e.g. 10 – 70 g, preferably 15 – 60 g, e.g. 20 – 50 g of the contrast substance, preferably barium sulphate, per 100 ml of suspension. The dose to be given to the patient depends on the case and is, for example, 10 – 2000 ml, e.g. 50 – 1000 ml, e.g. 100 – 500 ml of the suspension in X-ray investigations of the alimentary tract.

When using an X-ray contrast preparation in accordance with the present invention, extremely detailed X-ray pictures may be obtained of the body cavity being examined, for example of the intestinal tract, the walls of the body cavity being particularly well visibilized in a manner much more advantageous than has previously been possible, owing to the excellent properties of contrast agent with respect to its uniform adherence to the walls of said body cavity and to the length of time it remains adhered thereto. Thus, when using X-ray contrast preparations in accordance with the invention, extremely small tumours and other pathological conditions in the walls of the intestines can be shown, such pathological changes not being visible when effecting comparison tests with conventional barium sulphate contrast agents.

Compared with previously known contrast preparations for the X-ray examination of body cavities, the X-ray contrast preparation of the present invention is far less inclined to agglomerate in the gastro-intestinal tract and neither will it adhere to faeces to the same extent as do the known contrast agents, which markedly reduces the need of emptying the intestines prior to making an examination.

A common phenomenon with so-called double contrast examination of the intestines using conventional barium sulphate contrast preparations, is that the adherence of the contrast agent to the mucous membrane is impaired subsequent to air being injected, and will subsequently cease altogether. So-called crackling normally occurs within about 10 to 20 minutes, whereupon the examination must be interrupted in many cases.

It was found that during a period of one hour the ability of the contrast preparation according to the present invention to adhere to the mucous membrane was not impaired when air was injected into the patient. Owing to the fact that no crackling was found when using a preparation according to the invention, X-ray examinations could be carried out unhurriedly and with a high degree of diagnostic reliability.

Owing to the favourable results obtained when performing X-ray examinations using the X-ray contrast preparation according to the invention, the need to recall patients for re-examination was also reduced.

The invention will be described hereinafter with reference to a number of examples.

EXAMPLE 1

For the test there were used small, spherical waterinsoluble, but water-swellable, particles of dextran crosslinked with epichlorohydrin in alkaline solution to form a three-dimensional network, the water regain of which was 2,5 g of water per gram of cross-linked dextran, said network having subsequently been substituted with diethylaminoethyl groups with the aid of diethylaminoethyl chloride (a minor portion of the diethylaminoethyl groups being quaternized with diethylaminoethyl groups), and said particles being then converted into hydrochloride form (DEAE-Sephadex ® A 25, Pharmacia Fine Chemicals AB, Uppsala, Sweden). The particles used for the test were a screen fraction. In water swollen state, the particles have a particle size of approximately 60 μm. The particles contained about 3.5 milliequivalents of amino groups per gram of dry particles. The ion-exchange capacity of the particles for chloride ions was approximately 3.5 milliequivalents calculated per gram of dry particle. (The preparation of such ion exchangers are described, for example, in British Patent Specifications Nos. 936,039 and 1,013,585).

400 g of barium sulphate (having a particle size of about 0.1 – 5 μm) were thoroughly mixed with 850 ml of water and 50 g of the aforementioned polymer particles in dry form. The minute polymer particles were allowed to swell in the suspension whilst stirring the same. The suspension had a pH of about 7 and presented a good stability, even when stored. A great batch prepared similarly to that batch was placed in bottles of varying sizes from 10 ml to 2000 ml.

This X-ray contrast suspension was tested, inter alia, on rats and dogs. 2 ml of suspension were administered to each rat rectally. (The weight of the rats was about 200 g.) Owing to the manner in which the X-ray contrast agent adhered to and covered the mucous membrane of the intestines, the intestines were visibilized in a particularly advantageous manner, even subsequent to administering rectally to each rat 20 ml of air, to obtain so-called double contrast pictures. A large number of similar tests were also carried out on rats having experimentally developed tumours in the walls of the intestines, comparison tests also being made with aqueous suspensions of pure barium sulphate and commerically available conventional X-ray contrast preparations containing barium sulphate. The extent to which the contrast agent according to this Example adhered and covered the intestine walls and the tumours seated thereon was greater than that obtained with comparison agents. With the inventive contrast preparation, it was possible to visibilize much smaller tumours than could be visibilized with the comparison agents, and details with much smaller dimensions in the intestine walls could also be visibilized. This is of great value with respect to the diagnosis of tumours etc.

Similarly good X-ray pictures of the intestine were obtained when larger animals were administered rectally with quantities of the inventive X-ray contrast preparation adjusted according to the size of the animal and the type of examination being performed.

When the inventive X-ray contrast preparation was applied orally to rats and large animals, much better X-ray pictures of the oesophagus, the stomach and the intestines were obtained than with the conventional barium sulphate contrast preparations, owing to the superior ability of the X-ray agent to adhere to and to coat the walls of the body cavities. The X-ray pictures obtained with the inventive contrast agent were also more detailed than those attained with the conventional agent. Furthermore, smaller quantities of the contrast suspension are required than with conventional agents.

It was observed during the test that the contrast agent of the new preparation mixed readily with the content of the intestines. It could also be observed on the X-ray pictures that said contrast agent showed far less tendency or no tendency at all to adhere to said intestine contents, such as faeces. This is an advantage, since, inter alia, it reduces the necessity of emptying the intestines prior to performing an examination, and also reduces the risk that a further X-ray examination will be required. Crackling of the contrast agent in the intestines was not observed, either before or after administering air to the intestines, despite the fact that X-ray pictures were taken over a period of several hours. In the comparison tests the inventive contrast preparation was found to be far better than the conventional agent.

Thus, the aforedescribed inventive X-ray contrast agent preparation greatly improved the possibility of obtaining a reliable X-ray diagnosis of the intestines, and in addition reduces the necessity of making repeated X-ray examinations.

EXAMPLE 2

A contrast agent preparation produced in the same way as disclosed in Example 1, although with the difference that the polymer particles used in Example 1 were substituted with 50 g of such particles of the same size quaternized with propylene oxide in alkaline medium. (Screen fraction of QAE-Sephadex ®, Pharmacia Fine Chemicals AB, Uppsala, Sweden.) The particles contained about 3 milliequivalents of amino groups per gram of dry particles. The ion exchange capacity for chloride ions was, in respect of these particles, about 3 milliequivalents, calculated per gram of dry particles.

Tests, similar to those disclosed in Example 1, were made on animals. It was observed from the X-ray pictures that the contrast agent adhered still more strongly to the intestine walls, and the coating of contrast agent remained on said walls for a still longer period of time than with the test disclosed in Example 1.

EXAMPLE 3

The particles used in this example had been prepared as follows: 2.5 g of stearic acid were dissolved in 400 ml of 1,2-dichloroethane, 50 g of fine grained calcium carbonate, covered with 3 % of calcium stearate, were added. The mixture was stirred to give a homogeneous suspension. A mixture of 80 ml of tetraethylenepentamine, 2 g of calcium chloride and 60 ml of water was then added. The mixture was stirred vigorously and heated to 55° C. After 30 minutes 356 g of 1,4-butanedioldiglycide ether were added dropwise over a period of 30 minutes. The reaction was allowed to proceed with continued stirring until the small droplets had been converted to small gel beads. The gel beads were later washed well with water and then suspended twice in 0.1 N hydrochloric acid. They were then washed very carefully with water again by repeated slurrying in water. The product was sieved in order to remove the biggest particles, which were discarded. Then, a sieve fraction 25 μm – 80 μm was collected. The product was shrunk on a filter with ethanol, sucked off and dried in a vacuum drier at 50° C for two days. The mean particle size in water-swollen state was about 50 μm. One gram of the particles could absorb approximately 2 grams of water. The particles contained about 5 milliequivalents of amino groups per gram of dry particles.

400 g of barium sulphate (having a particle size of about 0.1 – 5 μm) were thoroughly mixed with 850 ml of water and 30 g of the dry polymer particles. This X-ray contrast suspension was tested, for example, rectally in rats as in Example 1. In the X-ray investigations it was observed that the contrast agent rapidly adhered and covered the intestinal walls very well. Very good X-ray pictures were obtained allowing more detailed studies of the intestinal wall as compared with conventional barium sulphate contrast preparations.

EXAMPLE 4

Contrast agent preparations prepared in the same way as disclosed in Example 1, although with the difference that as polymer particles were used varying quantities of (30 – 60 g) minute polymer particles containing amino groups, of the type described in the Swedish patent specifications Nos. 360,367 and 360,366, for example, obtained by cross-linking 1,6-diaminohexane or a mixture comprising meta- and para-xylylene diamine in the ratio 7:3 with epichlorohydrin or 1,4-butanedioldiglycide ether and also such gel particles in which the amino groups had been quaternized with propylene oxide in alkaline medium. Such particles may have a particle size of about 20 - 80 μm in water swollen state, and one gram of the dry particles may absorb about 2 - 10 ml of water, and one gram of the dry particles may contain 3 - 8 milliequivalents of amino groups.

EXAMPLE 5

40 g of tantalum powder (particle size about 1 - 5 μm) were mixed with 85 ml of water and 3.5 g of the same polymer particles as those disclosed in Example 1. Subsequent to being administered to rats rectally, good X-ray pictures of the intestine duct could be observed with good adhesion of the agent to the intestine walls.

What I claim is:

1. An X-ray contrast preparation intended for the X-ray examination of the gastro-intestinal tract, comprising minute particles of a cross-linked hydrophilic polymer containing amino groups suspended in a physiologically acceptable aqueous liquid and finely divided barium sulphate, said polymer being insoluble in water at body temperature and being a polyfunctional amine / or a member selected from the group consisting of dextran, cellulose, starch and pollulan which is substituted with amino groups and optionally with other ionizable groups which give rise to negative surface charges, said polymer having molecules held together to a water-insoluble, but waterswellable three-dimensional network by bridges comprising straight or branched aliphatic saturated hydrocarbon chains substituted by one or more hydroxyl groups and containing 3 - 30 carbon atoms and being non-broken or broken by one or more oxygen atoms and said polymer containing more than 0.1 and less than 15 milliequivalents of amino groups per gram of dry polymer, the swellability of the polymer particles in water being such that one gram of polymer in the presence of water is able to absorb more than 0.5 g and less than 50 g of water, the average particle size of the polymer particles in the presence of water being greater than 0.1 micrometer and smaller than 300 micrometer, and the ratio between the polymer particles and the barium sulphate being 2 to 100 g of said particles per 100 g of barium sulphate.

2. The X-ray contrast preparation according to claim 1, wherein the amino groups exist at least partially in the form of non-toxic salts.

3. The X-ray contrast preparation according to claim 1, wherein the surface layer of the minute particles contains only amino groups as ionizable groups.

4. The X-ray contrast preparation according to claim 1, wherein the surface layer of the minute polymer particles contains more amino groups than other ionizable groups.

5. A method of carrying out X-ray examination of the gastro-intestinal tract of a patient, which method comprises the oral or rectal administration to the patient of minute particles of a cross-linked hydrophilic polymer containing amino groups suspended in a physiologically acceptable aqueous liquid and finely divided barium sulphate and taking of pictures of the gastro-intestinal tract, said polymer being insoluble in water at body temperature and being a polyfunctional amine or a member selected from the group consisting of dextran, cellulose, starch and pollulan, which is substituted with amino groups and optionally with other ionizable groups which give rise to negative surface charges, said polymer having molecules held together to a water-insoluble, but water swellable threedimensional network by bridges comprising straight or branched aliphatic saturated hydrocarbon chains substituted by one or more hydroxyl groups and containing 3 - 30 carbon atoms and being non-broken or broken by one or more oxygen atoms and said polymer containing more than 0.1 and less than 15 milliequivalents of amino groups per gram of dry polymer, the swellability of the polymer in the presence of water is able to absorb more than 0.5 g and less than 50 g of water, the average particle size of the polymer particles in the presence of water being greater than 0.1 micro-meter and smaller than 300 micro-meter, and the ratio between the polymer particles and the barium sulphate being 2 to 100 g of said particles per 100 g of barium sulphate, the barium sulphate being used in an effective contrast-producing amount and the polymer particles being used in an effective amount for coating the surface of the parts of the gastro-intestinal tract to be examined.

6. The method of claim 5, wherein the amino groups exist at least partially in the form of non-toxic salts.

7. The method of claim 5, wherein the surface layer of the minute particles contains only amino groups as ionizable groups.

8. The method of claim 5, wherein the surface layer of the minute particles contains more amino groups than other ionizable groups.

* * * * *